(12) United States Patent
Schröder

(10) Patent No.: US 7,569,732 B2
(45) Date of Patent: Aug. 4, 2009

(54) CYCLISATION PROCESS

(75) Inventor: Fridtjof Schröder, Hettlingen (CH)

(73) Assignee: Givaudan SA, Vernler (CH)

( * ) Notice: Subject to any disclaimer, the term of this patent is extended or adjusted under 35 U.S.C. 154(b) by 0 days.

(21) Appl. No.: 11/816,006

(22) PCT Filed: Feb. 16, 2006

(86) PCT No.: PCT/CH2006/000102

§ 371 (c)(1),
(2), (4) Date: Oct. 10, 2007

(87) PCT Pub. No.: WO2006/086908

PCT Pub. Date: Aug. 24, 2006

(65) Prior Publication Data

US 2008/0114189 A1 May 15, 2008

(30) Foreign Application Priority Data

Feb. 21, 2005 (GB) .................. 0503528.2

(51) Int. Cl.
C07C 45/67 (2006.01)
C07C 49/21 (2006.01)
C07C 49/215 (2006.01)
A61K 8/18 (2006.01)

(52) U.S. Cl. .................. 568/341; 568/374; 512/24; 512/27

(58) Field of Classification Search ................ 568/374; 521/24, 27

See application file for complete search history.

(56) References Cited

U.S. PATENT DOCUMENTS 5,707,961 A * 1/1998 Bajgrowicz et al. ........... 512/17

FOREIGN PATENT DOCUMENTS

WO 2005016938 A1 2/2005

OTHER PUBLICATIONS

Bella M., et al."Chemistry of Odorants: stereoselective synthesis of octahydronaphthalene-based perfumery Georgywood{+,−)-1-[{1R<*>,2S<*>)-1,2,3,4,5,6,7,8-tetramethyln aphthale-2-y1] ethan-1one" Tetrahedron, Elsevier Science Publishers, Amsterdam, NL, vol. 60, No. 22, May 24, 2004, pp. 4821-4827, XP004508029 ISSN: 0040-4020.

* cited by examiner

Primary Examiner—Sikarl A Witherspoon
(74) Attorney, Agent, or Firm—Norris McLaughlin & Marcus, PA

(57) ABSTRACT

A process of preparation of cis-2-acetyl-1,2,3,4,5,6,7,8-octahydro-1,2,8,8-tetramethylnaphthalene ("β-Georgywood") from cis-1-[1,2-dimethyl-4(4-methyl-pent-3-enyl)-cyclohex-3-enyl]-ethanone ("Ψ-Georgywood"), comprising the reaction of Ψ-Georgywood with more than one molar equivalent of a Lewis acid. The method allows the preparation of isomeric mixtures that contain a much higher proportion of the olfactorily-desirable β-Georgywood than was previously possible.

13 Claims, No Drawings

CYCLISATION PROCESS

This is an application filed under 35 USC 371 of PCT/CH2006/000102.

This invention relates to a process of cyclisation promoted by Lewis acids, especially organoaluminium halides.

The compound cis-2-acetyl-1,2,3,4,5,6,7,8-octahydro-1,2,8,8-tetramethylnaphthalene (Formula I)

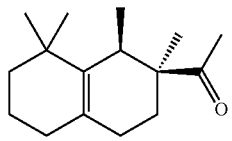

I (hereinafter β-GW), is the olfactorily most potent isomer of the commercialized fragrance mixture known as Georgywood (see Fráter, Müller and Schröder, "Tetrahedron" *Asymmetry*, 15 (2004), 3967-3972). ("Georgywood" is a trade mark of Givaudan S.A.).

The skilled person will realise that there are two enantiomers of β-GW. The one hereinabove shown as Formula I is the preferred enantiomer (it has the stronger fragrance), but the mixture of both enantiomers also has valuable properties. For the avoidance of doubt, all molecules depicted by structural formulae are, for the purposes of this invention, considered to cover both—the depicted enantiomer as well as the mixture of both enantiomers.

It is known that β-GW can be prepared by cyclisation of cis-1-[1,2-dimethyl-4(4-methyl-pent-3-enyl)-cyclohex-3-enyl]-ethanone (Formula II)

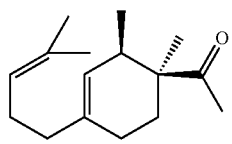

II (hereinafter Ψ-GW) using a Bronsted acid, such as $H_3PO_4$. Such a method is disclosed in U.S. Pat. No. 5,707,961. The problem with this method is that the product is a mixture of β-GW and the undesirable iso-Georgywood (hereinafter IGW—see Formula III), which cannot be converted to β-GW.

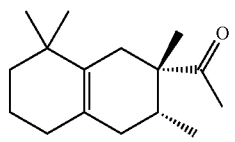

III

It is therefore desirable to increase the proportion of β-GW by avoiding the formation of IGW.

It has now been found that it is possible to carry out such a cyclisation reaction with the result being an enhanced proportion of β-GW in the final mixture. The invention therefore provides a process of preparation of β-GW from Ψ-GW, comprising the reaction of Ψ-GW with more than one molar equivalent of a Lewis acid in the absence of solvent or in the presence of a non-complexing solvent.

The product of this reaction is a mixture of β-GW, Georgywood-enolether (GWEE) (Formula IV) and γ-Georgywood (γ-GW—Formula V).

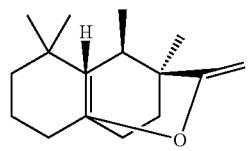

IV

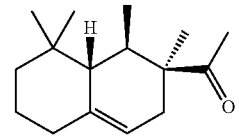

V

IGW may be present in a proportion of about 1-5% by weight, but it is generally completely absent.

This product mixture is very useful, as it can be converted to β-GW, as is hereinunder described.

The Lewis acids for use in this reaction may be selected from the group of $MX_n$-type Lewis acids with M=metal, X=halide and n=3-5. Preferred Lewis acids include (but are not limited to) $BBr_3$, $BCl_3$, $BF_3$, $AlBr_3$, $AlCl_3$, $ZrCl_4$, $ZrBr_4$, $TiCl_4$ and $TiBr_4$. A combination of such acids may be used; in this case the sum of the molar equivalents of each Lewis acid must be greater than 1.

Examples of non-complexing solvents include (but are not limited to) hydrocarbons, chlorinated hydrocarbons, nitroalkanes, toluene, chlorobenzene and cyclohexane. Naturally a mixture of two or more such solvents may be used.

The skilled person will be able to perform this reaction using the normal skill of the art known for the handling of Lewis acids. This includes water-free conditions under an atmosphere of argon or nitrogen, mixing of the reagents and substrates under cooling and conducting the reaction at a temperature typical for each Lewis acid, in case of the above-mentioned Lewis acids at temperatures between −50° C. and 0° C.

The GWEE/γ-GW/β-GW mixture thus obtained can be converted in a second acid-promoted cyclization step to pure β-GW. This is an advantage compared to the β-GW/IGW mixture of U.S. Pat. No. 5,707,961, where such a conversion is not possible. The overall yield of β-GW from Ψ-GW, however, does not exceed 45% (after distillation).

In a preferred embodiment of the invention, it has been found that the use of a particular class of Lewis acids brings substantial improvements in yield and selectivity. The invention therefore provides a process for the preparation of β-GW from Ψ-GW, comprising the reaction of Ψ-GW with more than two molar equivalents of an organoaluminium dihalide $RAlX_2$, where R is $C_1$-$C_3$ linear alkyl and X is Cl or Br, in the absence of solvent or in the presence of a non-complexing solvent.

The organoaluminium dihalide is preferably selected from the group consisting of methylaluminium dichloride (MADC), ethylaluminium dichloride (EADC) and methylaluminium sesquichloride (MASC). MADC is the preferred Lewis acid and may be prepared by any convenient method. However, specifically excluded from the class of MADCs useful in this invention is the crude reaction product prepared by the following method:

(i) reacting by heating a material of the formula $R_3Al_2X_3$, where R is $C_1$-$C_4$ alkyl and X is selected from bromine and iodine, with an aluminium-containing material selected from metallic aluminium and a mixture of metallic aluminium and aluminium trichloride in an atmosphere of methyl chloride, with the proviso that, when R is methyl and X is iodine, the aluminium-containing material is a mixture of aluminium and aluminium trichloride; and (ii) when the aluminium-containing material is metallic aluminium, adding aluminium trichloride to this reaction mixture and heating, to give a crude reaction product.

This method has already been disclosed in published International Application WO 2005/0016938 (PCT/CH2004/000505).

It has also been discovered that the organoaluminium dihalides hereinabove described can catalyse the cyclisation reaction, provided more than 1 molar equivalent of another Lewis acid is added to block the carbonyl group. The invention therefore additionally provides a process for the preparation of β-GW from Ψ-GW, comprising the reaction of Ψ-GW with a combination of aluminium chloride and a catalytic amount of organoaluminium dihalide, there being present one molar equivalent maximum of aluminium trichloride, the total of aluminium chloride and organoaluminium halide being greater than one molar equivalent.

It should be noted that, in this particular embodiment of the invention, the use of a crude MADC product, as described in WO 2005/0016938, is not excluded.

In a further embodiment of the invention, the organoaluminium dihalides may be also prepared in situ from trialkylaluminium compounds $AlR_3$ or dialkylaluminium halides $R_2AlX$ in the presence of $AlX_3$ (with R=$C_1$-$C_3$) and X=Br, Cl).

By "catalytic amount" is meant from 0.05-0.95 molar equivalents of the organoaluminium dihalide. Preferably 0.9-0.95 molar equivalents of $AlCl_3$ is employed in combination with 0.15-0.25 molar equivalents MADC. The reaction is carried out at elevated temperatures, preferably at 50° C., in non-complexing solvents (as described above), preferably toluene or chlorobenzene.

Conducting the reaction with aluminium chloride and catalytic amounts of MADC has the advantage that much less of the relatively expensive and hazardous MADC is needed, compared to the stoichiometric reaction with MADC alone, which needs at least 2 molar equivalents of this reagent. In addition, less of the greenhouse gas methane is produced during work-up and less aluminium wastes are generated.

This invention makes it possible to prepare mixtures of Georgywood that are much richer in the desirable β-GW than those previously obtained. The invention therefore also provides a Georgywood mixture that contains at least 70%, preferably from 85-95% β-GW, obtainable by a process as hereinabove described.

The invention is further described with reference to the following non-limiting examples, which describe preferred embodiments.

EXAMPLE 1

Cyclization of Ψ-GW with $AlCl_3$ followed by isomerization of the resulting β-, γ-, enolether-mixture to β-GW: cis-2-acetyl-1,2,3,4,5,6,7,8-octahydro-1,2,8,8-tetramethylnaphthalene:

2 g (8.5 mmol) Ψ-GW in 10 g toluene are cooled under nitrogen and stirring to −50° C., where $BBr_3$ (3.2 g, 13 mmol) are added dropwise via syringe. After 7 h at −50° C., 2 M HCl is added at this temperature. Back at 25° C. the mixture is extracted with t-butyl methyl ether. The organic phase is washed with $NaHCO_3$ and water until pH=7, dried over $MgSO_4$ and concentrated under reduced pressure. Bulb-to-bulb distillation at 90°-120°/0.05 Torr gives 1.1 g of a β-, γ-, enolether-mixture, which is dissolved in toluene and treated with p-toluenesulfonic acid (40 mg, 0.2 mmol). After 4 h at 100° C. the organic phase is washed with $Na_2CO_3$ and water until pH=7, dried and concentrated under reduced pressure giving 1.2 g of a brown oil, which is bulb-to-bulb distilled at 120° C./0.05 Torr giving 0.8 g (40%) β-GW with ~90% purity according to GC and NMR. IR (film): 2930 m, 1700 s (C=O), 1560 m, 1377 m, 1357 m, 1240 w, 1220 w, 1090 m. GC/MS: 234 (25%, [M]$^+$), 219 (15%, [M-$CH_3$]$^+$), 191 (100%, [M-Ac]$^+$, 161 (20%), 135 (65%), 121 (40%), 105 (40%), 91 (30%), 69 (30%), 43 (55%). $^1$H-NMR ($CDCl_3$, 400 MHz): 0.85 (d, 3H, J=6.9 Hz, Cl-Me), 0.99 (s, 3H), 1.02 (s, 3H), 1.06 (s, 3H), 1.4-2.2 (10 H, 5 $CH_2$), 2.15 (s, 3 H, Ac-Me), 2.36 (q, 1 H, J=6.9 Hz, Cl—H) ppm. $^{13}$C-NMR ($CDCl_3$, 400 MHz): 19.1 ($CH_2$), 19.7 ($CH_3$), 21.0 ($CH_3$), 22.5 ($CH_2$), 24.9 ($CH_3$), 27.7 ($CH_2$), 28.9 ($CH_3$), 29.4 ($CH_3$), 30.8 ($CH_2$), 34.0 (C), 35.4 (CH), 40.1 ($CH_2$), 50.7 (C), 125.9 (C=), 136.9 (C=), 214.5 (C=O) ppm.

EXAMPLE 2

Cyclization of Ψ- to β-GW with Commercial MADC 20 g (85 mmol) Ψ-GW dissolved in 100 g toluene is added under ice cooling to 157 g (0.21 mol) MADC (1 M in hexane). The mixture is heated to 70° C. for 2-3 h, then quenched under ice-cooling with 40 g ethanol, then with 2M HCl. The organic phase is separated and the aqueous phase extracted with t-butyl methyl ether. The combined organic layers are washed with conc. NaCl, then with water until pH=7. The organic phase is dried over $MgSO_4$, filtered and concentrated under reduced pressure. The residue is distilled over a short Vigreux column (124° C./0.1 Torr) to give 16 g (80%) of β-GW as a colorless liquid and a purity of ~90% according to GC and NMR. The analytical data of the product are consistent with the ones described in example 1.

EXAMPLE 3

Cyclization of Ψ- to β-GW with $AlCl_3$ and Catalytic Amounts of MADC 15 g (64 mmol) Ψ-GW dissolved in toluene (50 g) is added to a suspension of 8.1 g anhydrous $AlCl_3$ (61 mmol) in toluene (15 ml) under ice-cooling, nitrogen and stirring. After addition of MADC (16 ml, 16 mmol) in hexane (1 M) the brown-red solution is heated to 55° C. for 4 h. Work-up as described in example 2 and bulb-to-bulb distillation gives 10.5 g (70%) of β-GW as a colorless oil and a purity of 88% according to GC and NMR. The analytical data of the product are consistent with the ones described in example 1.

The invention claimed is:

1. A process for the preparation of cis-2-acetyl-1,2,3,4,5,6,7,8-octahydro-1,2,8,8-tetramethylnaphthalene ("β-GW") from cis-1-[1, 2-dimethyl-4-(4-methyl-pent-3-enyl)-cyclohex-3-enyl]-ethanone ("ΨGW"), comprising reacting Ψ-GW with more than one molar equivalent of a Lewis acid in the absence of solvent or in the presence of a non-complexing solvent.

2. A process according to claim 1, in which Ψ-GW is reacted with at least two molar equivalents of an organoaluminium dihalide RAlX$_2$, wherein:
R is linear C$_1$-C$_3$ alkyl and
X is Cl or Br,
in the absence of solvent or in the presence of a non-complexing solvent.

3. A process according to claim 2, in which the organoaluminium dihalide is selected from the group consisting of:
methylaluminium dichloride (MADC),
ethylaluminium dichloride (EADC) and
methylaluminium sesquichloride (MASC),
with the proviso that there is excluded the crude MADC prepared by the following method:
(i) reacting by heating a material of the formula R$_3$Al$_2$X$_3$, where R is C$_1$-C$_4$ alkyl and X is selected from bromine and iodine, with an aluminium-containing material selected from metallic aluminium and a mixture of metallic aluminium and aluminium trichloride in an atmosphere of methyl chloride, with the proviso that, when R is methyl and X is iodine, the aluminium-containing material is a mixture of aluminium and aluminium trichloride; and
(ii) when the aluminium-containing material is metallic aluminium, adding aluminium trichloride to this reaction mixture and heating, to give a crude reaction product.

4. A process according to claim 1, in which Ψ-GW is reacted with a combination of aluminium trihalide and a catalytic amount of organoaluminium dihalide, there being present one molar equivalent maximum of aluminium trihalide, the total of aluminium trihalide and organoaluminium halide being greater than one molar equivalent.

5. A process according to claim 4, in which the organoaluminium dihalide is prepared in situ from a trialkylaluminium compound AlR$_3$ or a dialkylaluminium halide R$_2$AlX, in which R is C$_1$-C$_3$ linear alkyl and X is chlorine or bromine, in the presence of AlX$_3$.

6. A process according to claim 1, in which the product of the reaction is a mixture of the compounds I, IV and V:

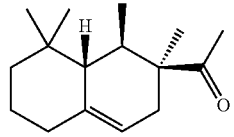

I

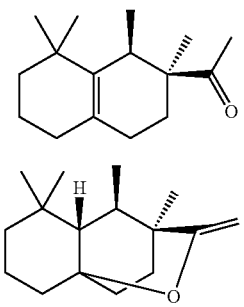

IV

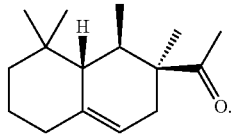

V which mixture is then further reacted in the presence of an acid to give a product with at least 70% compound of Formula I.

7. A mixture comprising at least 70% total of the compounds I, IV and V:

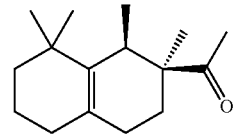

I

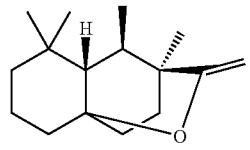

IV

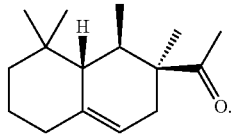

V

8. A process according to claim 1 for the preparation of a Georgywood mixture comprising at least 70% of β-GW.

9. A process according to claim 2 for the preparation of a Georgywood mixture comprising at least 70% of β-GW.

10. A process according to claim 3 for the preparation of a Georgywood mixture comprising at least 70% of β-GW.

11. A process according to claim 4 for the preparation of a Georgywood mixture comprising at least 70% of β-GW.

12. A process according to claim 5 for the preparation of a Georgywood mixture comprising at least 70% of β-GW.

13. A process according to claim 6 for the preparation of a Georgywood mixture comprising at least 70% of β-GW.

* * * * *